United States Patent [19]

Kino et al.

[11] Patent Number: 5,275,940
[45] Date of Patent: Jan. 4, 1994

[54] **PROCESS FOR PRODUCING L-TRYPTOPHAN BY CULTURING A *CORYNEBACTERIUM GLUTAMICUM* MUTANT**

[75] Inventors: Kuniki Kino, Hofu; Kazuhiro Furukawa, Yamaguchi; Yasuhiro Tomiyoshi, Ube; Yoshiyuki Kuratsu, Hofu, all of Japan

[73] Assignee: Kyowa Hakko Kogyo Co., Ltd., Tokyo, Japan

[21] Appl. No.: 748,559

[22] Filed: Aug. 22, 1991

[30] Foreign Application Priority Data

Aug. 30, 1990 [JP] Japan .................. 2-228715

[51] Int. Cl.⁵ .............................. C12P 13/22
[52] U.S. Cl. ................... 435/108; 435/252.1
[58] Field of Search ............... 435/108, 252.1

[56] References Cited

U.S. PATENT DOCUMENTS 4,601,982 10/1986 Shiio et al. ............... 435/108
4,618,580 7/1986 Shiio et al. ............... 435/108

FOREIGN PATENT DOCUMENTS 0128637 12/1984 European Pat. Off. .
1317395 7/1989 Japan .

OTHER PUBLICATIONS

Patent Abstract of Japan, vol. 5, No. 164 (C-76)(836) Oct. 21, 1981 & JP-A-56 092 796 (Ajinomoto K. K.) Jul. 27, 1981.

*Primary Examiner*—Douglas W. Robinson
*Assistant Examiner*—Marian C. Knode
*Attorney, Agent, or Firm*—Antonelli, Terry, Stout & Kraus

[57] ABSTRACT

Disclosed is a process for producing L-tryptophan which comprises culturing in a medium a microorganism belonging to the genus Corynebacterium or Brevibacterium having resistance to an aminoquinoline derivative or a phenothiazine derivative and an ability to produce L-tryptophan until L-tryptophan is accumulated in the culture and recovering L-tryptophan therefrom.

1 Claim, No Drawings

PROCESS FOR PRODUCING L-TRYPTOPHAN BY CULTURING A *CORYNEBACTERIUM GLUTAMICUM* MUTANT

BACKGROUND OF THE INVENTION

The present invention relates to a process for producing L-tryptophan by culturing a microorganism belonging to the genus Corynebacterium or Brevibacterium, and having resistance to an aminoquinoline derivative or a phenothiazine derivative and an ability to produce L-tryptophan. L-Tryptophan is an amino acid which is useful as a medicament or as food and an additive for animal feed.

Heretofore, various processes for producing L-tryptophan by culturing a Coryneform gultamic acid-producing bacterium are known; for example, a process by use of a microorganism belonging to the genus Corynebacterium, requiring L-tyrosine and L-phenylalanine for growth and having resistance to at least one of tyrosine analogs and phenylalanine analogs (Japanese Published Examined Patent Application No. 19037/76); a process by use of a microorganism having resistance to a tryptophan analog such as 5-methyltryptophan, etc. (Japanese Published Examined Patent Application Nos. 18828/73, 38795/76 and 39517/78); a process by use of a histidine auxotroph (Japanese Published Examined Patent Application No. 4505/72); a process by use of a microorganism belonging to the genus Brevibacterium which is decreased or lacking in pyruvate kinase activity (Japanese Published Unexamined Patent Application No. 253391/87); a process by use of a microorganism belonging to the genus Corynebacterium which is decreased or lacking in phosphoenolpyruvate carboxylase activity (Japanese Published Unexamined Patent Application No. 317395/89); etc. An efficient process for producing L-tryptophan is always in demand from an industrial view point.

SUMMARY OF THE INVENTION

According to the present invention, L-tryptophan can be produced in high yields at lower costs by culturing in a medium a microorganism belonging to the genus Corynebacterium or Brevibacterium, and having resistance to an aminoquinoline derivative or a phenothiazine derivative and an ability to produce L-tryptophan until L-tryptophan is accumulated in the culture, and recovering L-tryptophan therefrom.

DETAILED DESCRIPTION OF THE INVENTION

The aminoquinoline derivative refers to a compound having an aminoquinoline skeleton and includes, for example, a 4-aminoquinoline derivative such as chloroquine, amodiaquine, etc., an 8-aminoquinoline derivative such as primaquine, pentaquine, etc. Salts such as phosphate, hydrochloride, etc. of these compounds may also be used. These compounds are all known as antimalarial drugs.

The phenothiazine derivative refers to a compound having a phenothiazine skeleton and includes, for example, phenothiazine, a phenothiazine derivative having a dimethylamino side chain such as promazine, chlorpromazine, promethazine, etc. Salts such as hydrochloride, etc. of these compounds may also be used. These compounds are all known as antipsychotic drugs.

As the microorganism used in the present invention, any microorganism may be used so long as it belongs to the genus Corynebacterium or Brevibacterium which are known to be a Coryneform glutamic acid-producing bacterium, and has an ability to produce L-tryptophan and resistance to an aminoquinoline derivative or a phenothiazine derivative.

The L-tryptophan-producing microorganism having resistance to an aminoquinoline derivative or a phenothiazine derivative may be obtained by imparting the aminoquinoline derivative- or phenothiazine derivative- resistance to a known L-tryptophan-producing microorganism. Reversibly, the L-tryptophan-producing microorganism having resistance to an aminoquinoline derivative or a phenothiazine derivative may also be obtained by imparting mutation of improving L-tryptophan productivity such as auxotrophy, analog resistance, etc. to a mutant having resistance to an aminoquinoline derivative or a phenothiazine derivative derived from a wild strain. The L-tryptophan-producing mutant may be selected as a strain requiring L-tyrosine or L-phenylalanine for growth, or having amino acid analog-resistance [Journal of Agricultural Chemical Association, 50 (1), p.R79 (1976)].

The mutant having resistance to an aminoquinoline derivative or a phenothiazine derivative in the present invention may be obtained by applying a conventional mutation technique such as UV irradiation and a chemical treatment with N-methyl-N'-nitro-N-nitrosoguanidine (hereafter referred to as NTG), nitric acid, etc.; and such resistant mutant is selected as a strain which can grow in an agar plate medium containing an aminoquinoline derivative or a phenothiazine derivative in such a concentration that the parent strain cannot grow.

Specific examples of the L-tryptophan-producing microorganism having resistance to an aminoquinoline derivative or a phenothiazine derivative include primaquine-resistant *Corynebacterium glutamicum* H-7853, chloroquine-resistant *Corynebacterium glutamicum* H-7854 and promazine-resistant *Corynebacterium glutamicum* H-8014, etc. These strains have been deposited, under the Budapest Treaty, with the Fermentation Research Institute of the Agency of Industrial Science and Technology of Japan since Aug. 10, 1990 with accession numbers, FERM BP-3055, FERM BP-3056 and FERM BP-3057, respectively.

According to the present invention, production of L-tryptophan can be effected by culturing the above microorganism in a conventional manner. As the medium used, any synthetic or natural medium may be used so long as it appropriately contains carbon sources, nitrogen sources, inorganic compounds and trace amounts of other nutrients required for the strain used.

As the carbon sources, carbohydrates such as glucose, glycerol, fructose, sucrose, maltose, mannose, starch, starch hydrolyzate, molasses, polyalcohol, etc.; and various organic acids such as pyruvic acid, fumaric acid, lactic acid, acetic acid, etc. can be used. Depending upon assimilability of a microorganism to be used, hydrocarbons, alcohols, etc. may also be used. In particular, blackstrap molasses is preferably used.

As the nitrogen sources, ammonia; various inorganic and organic ammonium salts such as ammonium chloride, ammonium sulfate, ammonium carbonate, ammonium acetate, etc.; urea and other nitrogen-containing compounds, nitrogen-containing organic material such as peptone, NZ-amine, meat extract, yeast extract, corn steep liquor, casein hydrolyzate, fish meal or its digested product, etc. can be used.

As the inorganic compounds, potassium dihydrogen phosphate, dipotassium hydrogen phosphate, ammonium sulfate, ammonium chloride, magnesium sulfate, sodium chloride, ferrous sulfate, manganese sulfate, calcium carbonate, etc. can be used.

Culturing is carried out under aerobic conditions such as shaking culture, submerged culture with aeration, etc. The temperature for the culturing is preferably in a range of 20° to 40° C. The pH of the medium is maintained preferably around neutrality during the culturing. The culturing is generally completed in 1 to 5 days.

After the completion of culturing, precipitates such as cells, etc. are removed from the culture and L-tryptophan can be recovered from a supernatant by a known technique such as crystallization concentration, a treatment with activated carbon or a treatment with ion-exchange resin, etc.

Hereafter the present invention is specifically described with reference to the examples.

EXAMPLE 1

Acquirement of the Mutant Strain of the Present Invention

*Corynebacterium glutamicum* BPS-13 (FERM BP-1777 Japanese Published Unexamined Patent Application No. 317395/89) having an ability to produce L-tryptophan was used as the parent strain. After culturing at 30° C. for 16 hours in a complete medium (a medium containing 20 g of bouillon powders and 5 g of yeast extract in 1 liter of water, pH adjusted to 7.2), the cells were collected and washed with 0.05M phosphate buffer (pH 7.2). The cells were then suspended in the buffer in a cell concentration of about $10^9$ cells/ml. NTG was added to the suspension in a final concentration of 500 μg/ml, and the mixture was allowed to stand at 30° C. for 20 minutes to effect mutation. After the cells were washed with the buffer, the cells were spreaded on an agar plate medium containing 0.2 mM primaquine phosphate and having a composition shown in Table 1.

TABLE 1

| Composition of Minimum Medium | |
|---|---|
| Glucose | 10 g/l |
| (NH$_4$)H$_2$PO$_4$ | 1 g/l |
| KCl | 0.2 g/l |
| MgSO$_4$.7H$_2$O | 0.2 g/l |
| FeSO$_4$.7H$_2$O | 10 mg/l |
| MnSO$_4$.4~6H$_2$O | 0.2 mg/l |
| ZnSO$_4$.7H$_2$O | 0.9 mg/l |
| CuSO$_4$.5H$_2$O | 0.4 mg/l |
| Na$_2$B$_4$O$_7$.10H$_2$O | 0.09 mg/l |
| (NH$_4$)$_6$Mo$_7$O$_{24}$.4H$_2$O | 0.04 mg/l |
| Biotin | 50 μg/l |
| p-Aminobenzoic acid | 2.5 mg/l |
| Thiamine hydrochloride | 1 mg/l |
| L-tyrosine | 50 mg/l |
| L-phenylalanine | 50 mg/l |
| Agar | 16 g/l |
| | (pH 7.2) |

After culturing at 30° C. for 5 to 10 days, large colonies grown on the agar plate medium were picked up and subjected to the L-tryptophan production test. A mutant having a higher L-tryptophan productivity than that of *Corynebacterium glutamicum* BPS-13 was selected. The selected strain was named as *Corynebacterium glutamicum* H-7853, which is resistant to primaquine. In a similar manner the same procedure as in the acquirement of the primaquine-resistant mutant was repeated except that 0.3 mM chloroquine phosphate or 0.3 mM promazine hydrochloride was contained in the medium in place of 0.2 mM primaquine phosphate. Thus, chloroquine-resistant mutant *Corynebacterium glutamicum* H-7854 and promazine-resistant mutant *Corynebacterium glutamicum* H-8014 were obtained.

The thus obtained mutants and the parent strain (BPS-13) were compared with each other with respect to drug resistance. The results are shown in Tables 2, 3 and 4. That is, each strain was cultured at 30° C. for 24 hours in the complete medium described above. The cells were suspended in a physiological saline in a cell concentration of about $10^4$ cells/ml. 0.1 ml of the suspension was spreaded on the agar plate medium which is identified in Table 1 containing primaquine phosphate, chloroquine phosphate or promazine hydrochloride at the concentrations shown in Tables 2, 3 and 4. After culturing at 30° C. for 7 days, drug resistance was determined by the degree of growth.

The results indicate that growth of the mutants was not inhibited by the drugs in such a concentration that the parent strain could not grow, which shows that the mutants acquire strong resistance to each drug.

TABLE 2

| | Primaquine Phosphate (mM) | | | |
|---|---|---|---|---|
| Strain | 0 | 0.1 | 0.15 | 0.2 |
| BPS-13 | ++ | − | − | − |
| H-7853 | ++ | ++ | + | ± |

TABLE 3

| | Chloroquine Phosphate (mM) | | | |
|---|---|---|---|---|
| Strain | 0 | 0.1 | 0.2 | 0.3 |
| BPS-13 | ++ | + | ± | − |
| H-7854 | ++ | ++ | ++ | + |

TABLE 4

| | Promazine Hydrochloride (mM) | | | |
|---|---|---|---|---|
| Strain | 0 | 0.1 | 0.2 | 0.3 |
| BPS-13 | ++ | − | − | − |
| H-8014 | ++ | ++ | + | ± |

++ : sufficient growth
+ : moderate growth
± : poor growth
− : no growth

EXAMPLE 2

L-tryptophan Production Test

*Corynebacterium glutamicum* H-7853, H-7854 and H-8014 obtained in Example 1 and the parent strain BPS-13 were inoculated into 20 ml of a seed medium comprising 2% glucose, 1.5% polypeptone, 1.5% yeast extract, 0.25% sodium chloride, 0.1% urea, 200 mg/l L-tyrosine and 200 mg/l L-phenylalanine, (pH 7.2) charged in an Erlenmeyer's flask of 250 ml volume, and cultured with shaking at 30° C. for 24 hours on a rotary shaker at 210 r.p.m. (revolutions per minute). After 2 ml of the resulting seed culture was inoculated into 20 ml of a fermentation medium having the following composition charged in an Erlenmeyer's flask of 250 ml volume and culturing was carried out for 72 hours in a manner similar to the procedures for the seed culture. Composition of the fermentation medium:

6% glucose, 0.05% KH$_2$PO$_4$, 0.05% K$_2$HPO$_4$, 0.025% MgSO$_4$.7H$_2$O, 0.025% ammonium sulfate, 30

μg/l biotin, 10 mg/l MnSO$_4$.7H$_2$O, 0.5% corn steep liquor, 2% CaCO$_3$ (pH 7.2)

After the completion of the culturing, the amount of L-tryptophan accumulated was quantitatively determined by high performance liquid chromatography.

The results are shown in Table 5.

TABLE 5

| Strain | L-Tryptophan (g/l) |
|---|---|
| BPS-13 | 7.2 |
| H-7853 | 8.7 |
| H-7854 | 8.2 |
| H-8014 | 8.6 |

2 liters of the L-tryptophan-containing fermentation broth obtained by culturing H-7853 strain was centrifuged to remove the cells, calcium carbonate and other impurities. The obtained supernatant was passed through a column packed with strongly acidic cation exchange resin Diaion SK-104 (H$^+$ type) (product of Mitsubishi Kasei Corporation, Japan) to adsorb L-tryptophan thereto. After the column was washed with water, the column was eluted with 0.5N aqueous ammonia. The eluate was desalted and the resulting crude L-tryptophan crystalline powders were dissolved in a small quantity of 50% hot ethanol. The solution was treated with activated carbon for decoloration. After cooling, 12.2 g of L-tryptophan crystals was obtained.

What is claimed is:

1. A process for producing L-tryptophan which comprises culturing in a nutrient medium a microorganism which is selected from the group consisting of *Corynebacterium glutamicum* FERM BP-3055 having resistance to primaquine, *Corynebacterium glutamicum* FERM BP-3056 having resistance to chloroquine and *Corynebacterium glutamicum* FERM BP-3057 having resistance to promazine until L-tryptophan is accumulated in the culture, and recovering L-tryptophan therefrom.

* * * * *